(12) United States Patent
Jakobsen

(10) Patent No.: US 11,400,227 B2
(45) Date of Patent: Aug. 2, 2022

(54) END-OF-CONTENT MECHANISM

(71) Applicant: Novo Nordisk A/S, Bagsvaerd (DK)

(72) Inventor: Nikolaj Eusebius Jakobsen, Soeborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 97 days.

(21) Appl. No.: 16/500,991

(22) PCT Filed: Apr. 6, 2018

(86) PCT No.: PCT/EP2018/058916
§ 371 (c)(1),
(2) Date: Oct. 4, 2019

(87) PCT Pub. No.: WO2018/185317
PCT Pub. Date: Oct. 11, 2018

(65) Prior Publication Data
US 2020/0030542 A1    Jan. 30, 2020

(30) Foreign Application Priority Data
Apr. 7, 2017 (EP) .................................. 17165541

(51) Int. Cl.
*A61M 5/315* (2006.01)
*A61M 5/31* (2006.01)

(52) U.S. Cl.
CPC .... *A61M 5/31546* (2013.01); *A61M 5/31593* (2013.01); *A61M 2005/3126* (2013.01)

(58) Field of Classification Search
CPC .......... A61M 5/31546; A61M 5/31593; A61M 2005/3125; A61M 2005/3126
See application file for complete search history.

(56) References Cited

U.S. PATENT DOCUMENTS

| | | | |
|---|---|---|---|
| 9,022,991 B2 | 5/2015 | Moeller | |
| 2008/0234633 A1* | 9/2008 | Nielsen | A61M 5/24 604/208 |

(Continued)

FOREIGN PATENT DOCUMENTS

| | | |
|---|---|---|
| EP | 1095668 B1 | 4/2007 |
| JP | 2012512675 A | 6/2012 |
| WO | 90/09202 | 8/1990 |
| WO | 01/19434 A1 | 3/2001 |
| WO | 2009132778 A1 | 11/2009 |
| WO | 2015165991 A1 | 11/2015 |

*Primary Examiner* — Dung T Ulsh
(74) *Attorney, Agent, or Firm* — Wesley Nicolas

(57) ABSTRACT

The present invention provides a drug injection device (1) for delivering multiple doses of drug, comprising: a housing (2) extending along a main axis, a dose expelling mechanism comprising a piston rod (60) configured to move relative to the housing (2) from a first position to a second position to cause ejection of a dose of drug, the piston rod (60) extending between a proximal piston rod end and a distal piston rod end and comprising a dosing track (63), the piston rod (60) further being movable relative to the housing (2) from an initial pre-use position to a final end stop position to cause accumulated ejection of a predefined total dose, a dosing track follower (17) fixed with respect to the housing (2) and adapted to travel the dosing track (63) during dose ejection, a dose setting mechanism operable to set the dose to be ejected by the dose expelling mechanism, electronic means (82, 90, 91, 92, 95) for registering a dose setting operation and for registering a dose size of an ejected dose, and a display (81) adapted to indicate a size of a current set dose, the electronic means (82, 90, 91, 92, 95) being configured to provide a first type of update of the display (81) responsive to dose changing operations of the dose setting mechanism, wherein the electronic means (82, 90, 91, 92, 95) is further configured to calculate a current (Continued)

accumulated dose from the dose sizes of registered ejected doses to thereby provide an updated value of a total amount of drug ejected, determine a current remaining dose by comparing the current accumulated dose and the predefined total dose, and provide a second type of update of the display (81) when during a dose increasing operation of the dose setting mechanism the current set dose exceeds the current remaining dose, the second type of update being different from the first type of update, and wherein the final end stop position is defined by a track end configuration of the dosing track (63) between the proximal piston rod end and the distal piston rod end.

11 Claims, 4 Drawing Sheets

(56) References Cited

U.S. PATENT DOCUMENTS

| | | | | |
|---|---|---|---|---|
| 2008/0234634 A1* | 9/2008 | Eiland | ............... | A61M 5/31583 |
| | | | | 604/208 |
| 2008/0287883 A1* | 11/2008 | Radmer | ............ | A61M 5/31545 |
| | | | | 604/211 |
| 2012/0103328 A1 | 5/2012 | Smith et al. | | |
| 2013/0041257 A1* | 2/2013 | Nemoto | ................. | A61B 6/507 |
| | | | | 600/432 |
| 2014/0142511 A1* | 5/2014 | Gilmore | ................... | G01D 5/25 |
| | | | | 604/189 |
| 2014/0142512 A1* | 5/2014 | Butler | ............... | A61M 5/31585 |
| | | | | 604/189 |
| 2016/0263327 A1 | 9/2016 | Radmer et al. | | |

\* cited by examiner

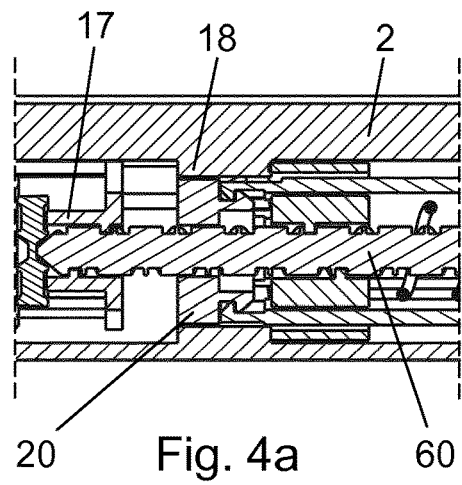
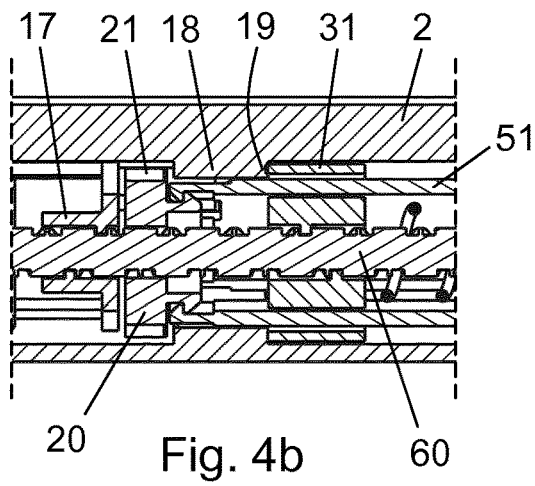
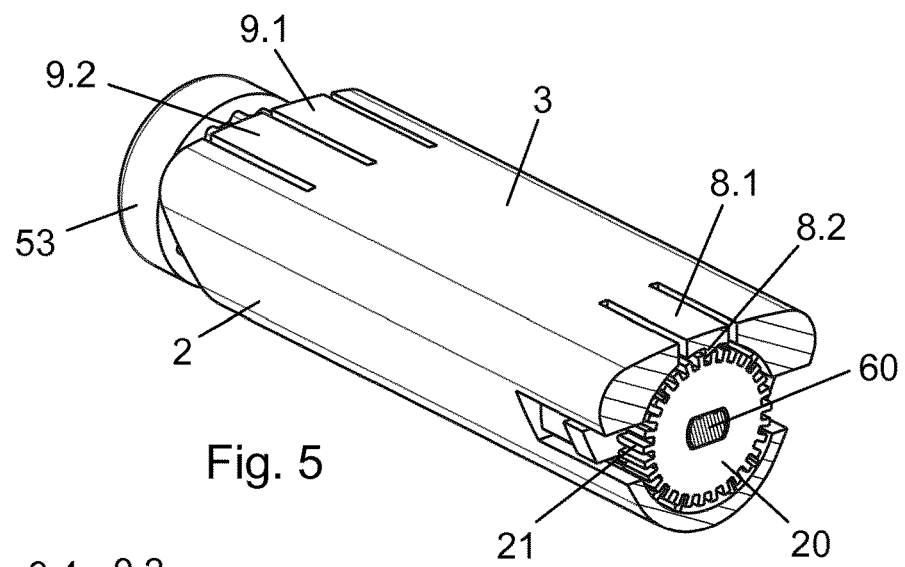
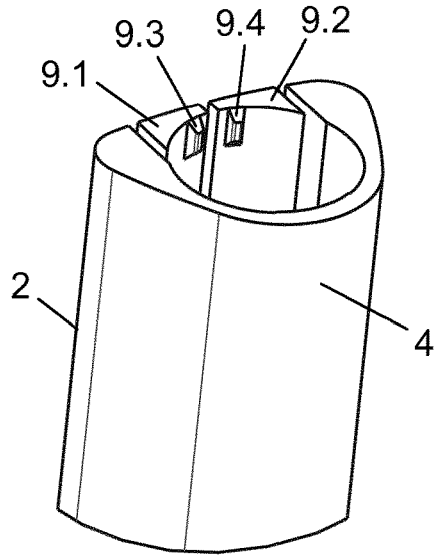
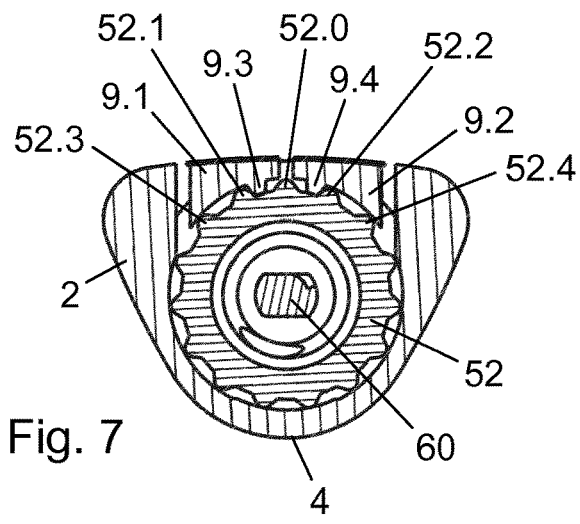

END-OF-CONTENT MECHANISM

CROSS-REFERENCE TO RELATED APPLICATIONS

This application is a 35 U.S.C. § 371 National Stage application of International Application PCT/EP2018/058916 (published as WO 2018/185317), filed Apr. 6, 2018, which claims priority to European Patent Application 17165541.8, filed Apr. 7, 2017, the contents of all above-named applications are incorporated herein by reference.

FIELD OF THE INVENTION

The present invention relates generally to devices for administering medicine to a subject, and more specifically to injection devices capable of setting and expelling one or more doses of drug from a drug reservoir.

BACKGROUND OF THE INVENTION

In the diabetes care segment parenteral drug administration carried out using a traditional vial and syringe system is increasingly being substituted by administration using a pen injection device. Pen injection devices are particularly convenient in that they allow the user to perform a dosed injection from a prefilled drug reservoir without first having to manually transfer the particular dose from one reservoir (the vial) to another (the syringe).

Predominantly, two types of pen injection devices are available, durable injection devices being capable of delivering one or more doses of drug from a prefilled drug cartridge which can be loaded into the device before use and replaced after exhaustion, and disposable injection devices being capable of delivering one or more doses of drug from a prefilled and non-exchangeable drug cartridge. Each of these types of pen injection devices are, or may in principle be, realised in various sub-types, such as e.g. single shot devices adapted to deliver only one dose from a drug cartridge, multi-shot devices capable of delivering a plurality of doses from a drug cartridge, manual devices, where the user provides the force needed for injection, automatic devices having a built-in energy source releasable to occasion the injection, fixed dose devices adapted to deliver a predetermined dose of drug, variable dose devices offering delivery of different doses of drug, settable by the user, etc.

As the labels suggest a durable injection device is intended for use over a considerable period of time during which multiple drug cartridges are exhausted and replaced, whereas a disposable injection device is intended for use until its dedicated drug cartridge is exhausted, after which the entire injection device is discarded.

Multi-shot devices can be of the fixed dose type or the variable dose type, and the drug expelling mechanisms in such devices can be mechanical, i.e. where movements of the piston rod are controlled mechanically, such as in manual devices or spring-driven devices, or electro-mechanical, i.e. where movements of the piston rod are controlled electronically, such as in electro-motor driven devices.

A valued feature of certain multi-shot devices is the so-called end-of-content mechanism, which prevents a user from setting a dose of a size exceeding the amount of drug remaining in the drug cartridge. Thereby, the user is prevented from accidentally underdosing and consequently ending up in a potentially dangerous situation.

WO 01/19434 (Novo Nordisk A/S) discloses respective examples of end-of-content mechanisms for different types of injection devices, where a track following geometry is adapted to follow a track during dose setting, and where the length of the track is correlated with the total amount of drug expellable from the employed drug cartridge. The dose setting is performed by rotation of a dose setting member relative to a housing, and a mechanical coupling between the dose setting member and the track following geometry ensures that the degree of rotation of the dose setting member is correlated with the travel of the track following geometry along the track. When the track following geometry reaches the end of the track the dose setting member is stopped and a tactile feedback is thus produced indicating to the user that a dose setting limit is reached.

One potential issue with such solutions is that if the user does not realise that the resistance to further rotation of the dose setting member is due to the end-of-content mechanism he or she may increase the torque on the dose setting member in the expectation of overcoming the obstacle and thus cause breakage of one or more components in the device. In order to prevent this, the device needs to be of a sufficiently robust build and/or provided with an over-torque protection mechanism, e.g. in the form of a slip coupling. The former inevitably adds to the size of the device, while the latter requires an additional mechanical construction which adds costs to the manufacturing.

In view hereof it is desirable to devise an end-of-content mechanism for an injection device which does not add significantly to the size and/or manufacturing cost of the device.

SUMMARY OF THE INVENTION

It is an object of the invention to eliminate or reduce at least one drawback of the prior art, or to provide a useful alternative to prior art solutions.

In particular, it is an object of the invention to provide an injection device having an end-of-content mechanism which does not need to be able to resist or manage large dose setting torques.

It is a further object of the invention to provide an injection device having an end-of-content mechanism which enables a slim device design.

It is an even further object of the invention to provide an injection device having an end-of-content mechanism which can be realised by use of few mechanical components.

It is an even further object of the invention to provide an end-of-content mechanism for a cost-effective injection device offering electronic detection of set and injected doses.

In the disclosure of the present invention, aspects and embodiments will be described which will address one or more of the above objects and/or which will address objects apparent from the following text.

Thus, in a first aspect the invention provides a drug injection device according to claim 1.

Thereby, an injection device of the type which is capable of electronically registering set doses and ejected doses from a present drug cartridge is provided. The injection device comprises a housing extending along a main axis, a dose setting mechanism operable to set a dose to be ejected, a display for indicating a size of a current set dose, and a dose expelling mechanism comprising a piston rod configured to move relative to the housing from a first position to a second position to cause ejection of a selected dose. The piston rod is movable relative to the housing from an initial pre-use position to a final end stop position to cause accumulated ejection of a predefined total dose, i.e. during the very first drug expelling action the piston rod moves relative to the housing from the initial pre-use position to a dose delivered position which is determined by the size of the first expelled dose, during the second drug expelling action the piston rod moves further relative to the housing in accordance with the size of the second set dose, and during the last drug expelling action the piston rod reaches the final end stop position, which physically prevents it from moving further in the drug expelling direction, and over the cause of these plurality of drug expelling actions an accumulated volume of drug which is correlated with the predefined accumulated movement of the piston rod from the initial pre-use position to the final end stop position is delivered from the present drug cartridge. The initial pre-use position is predetermined during manufacturing when the piston rod is being arranged in the housing.

The injection device further comprises electronic means, e.g. including processing means and memory means, configured to a) prompt the display to provide a first type of update to an indication of the size of the current set dose in response to a dose changing operation of the dose setting mechanism, b) calculate a current accumulated dose from registered ejected doses, thereby providing an updated value of a total amount of drug ejected from the injection device, c) determine a current remaining dose by comparing the current accumulated dose and the predefined total dose, and d) prompt the display to provide a second type of update to the indication of the size of the current set dose if during a dose increasing operation of the dose setting mechanism the current set dose exceeds the current remaining dose, where the second type of update differs from the first type of update.

The piston rod extends between a proximal piston rod end and a distal piston rod end and comprises a dosing track, and the injection device further comprises a dosing track follower fixed with respect to the housing and adapted to travel the dosing track during dose ejection. The dosing track follower may e.g. form part of the housing or form part of an element which is axially and rotationally fixed relative to the housing.

The final end stop position is defined by a track end configuration, such as a termination, of the dosing track between the proximal piston rod end and the distal piston rod end. The piston rod is thereby physically prevented from further axial movement relative to the housing when the dosing track follower reaches the track end configuration of the dosing track. The track end configuration is arranged at a specific position along the piston rod which correlates an accumulated travel of the dosing track follower from a predetermined pre-use position in or on the dosing track to the track end configuration with an expelling of the predefined total dose.

The injection device may comprise a drug cartridge when supplied from the manufacturer, or it may comprise means for receiving a drug cartridge, as e.g. provided by the user. The drug cartridge may comprise a cylindrical cartridge body being closed at one end by a piston and at the other end by a penetrable septum.

The dose expelling mechanism may be mechanical, which provides for a less expensive solution than an electro-motor based dose expelling mechanism. Furthermore, the electronic means and the display may be provided in the form of printed electronics, which can be realised and applied in a relatively inexpensive manner, enabling a cost-effective end product.

In an injection device of the above described type by calculating the current accumulated dose from registered ejected doses the processing means keeps track of the total amount of drug that has been expelled from the drug cartridge, and by repeatedly determining the current remaining dose based on the current accumulated dose and the predefined total dose, which is a pre-programmed target dose, the electronic means is capable of responding immediately when the user during a dose setting action operates the dose setting mechanism so as to set a dose which exceeds the current remaining dose.

Such an injection device is thus able to alert the user to the dose setting limit without having to rely on a mechanical stop interface in the dose setting mechanism. The display will provide the information that a dose exceeding the remaining dose has been set, and even though the user may choose to disregard this information and execute a drug expelling action anyway the actually ejected dose of drug will not exceed the dose indicated on the display because of the incorporated mechanical stop in the dose expelling mechanism being correlated with the predefined total dose which is deliverable from the drug cartridge.

Hence, by relying solely on an electronic end-of-content indication the requirement of a dose setting mechanism which is able to handle large torques is rendered superfluous, allowing for a slender and attractive device design, that may fit in a pocket, a small handbag, or the like and/or an end product with fewer mechanical parts.

The first type of update may comprise an incremental increase or decrease of the size of the current set dose, depending on whether the dose changing operation of the dose setting mechanism is a dose increasing or a dose decreasing operation. For example, the first type of update may comprise replacing a currently displayed number with a first new number being one unit higher, if the dose setting mechanism is operated to increase the current set dose by one unit, and replacing the currently displayed number with a second new number being one unit lower, if the dose setting mechanism is operated to decrease the current set dose by one unit.

The second type of update may comprise a freeze of the indication of the size of the current set dose, i.e. in fact a lack of update of the display of the indication of the size of the current set dose. If, for example, the display shows the size of the current set dose as a number, this number will remain on display as long as the current set dose exceeds the current remaining dose. The user will then notice when a dose increasing dose setting operation no longer leads to a change of the displayed dose and will thus know that the frozen number represents the remaining expellable dose.

Alternatively, or additionally, the second type of update may comprise a change of form, position and/or colour of the indication of the size of the current set dose relative to previously displayed indications of the size of the current set dose. Any of such sudden deviations from the previous display updates will alert the user to the fact that the dose setting limit has been exceeded.

Alternatively, or additionally, the second type of update may comprise an enabling of an otherwise disabled symbol on the display, i.e. a sudden appearance of the symbol on the display.

Alternatively, or additionally, the second type of update comprises an indicator being alternatingly visible and invisible.

The electronic means may further comprise means for providing a tactile, e.g. vibratory, and/or audible signal in response to the current set dose exceeding the current remaining dose to thereby enhance the response from the injection device Importantly, the processing means may detect any dose changing operation of the dose setting mechanism, regardless of whether the dose setting limit has been exceeded or not. So, the processing means may be further configured to prompt the display to provide the first type of update when during a dose decreasing operation of the dose setting mechanism the current set dose falls below the current remaining dose.

Thereby, the display will indicate reductions of the current set dose in the same manner as before as soon as the current set dose has been decreased below the level of the current remaining dose determined by the processing means, allowing the user to check the current remaining dose at any point before the last drug expelling action and to set and eject any selectable dose which does not exceed the current remaining dose.

The electronic means may calculate the current accumulated dose by adding up a most recently registered dose size of an ejected dose and each previously registered dose size, or by adding said most recently registered dose size of an ejected dose to a most recently calculated accumulated dose.

The electronic means may determine the current remaining dose by subtracting the current accumulated dose from the predefined total dose. This provides a value which can subsequently be compared directly with the value of the current set dose to determine whether the user has set a too large dose. Alternatively, the electronic means may determine the current remaining dose without actually calculating a value of the current remaining dose, e.g. by comparing a value or level representing a current sum of the current accumulated dose and the current set dose with a value or level representing the predefined total dose.

The dose setting mechanism may comprise a user operable dose setting button and a dose setting element rotationally locked with respect to the dose setting button and adapted to undergo helical movement relative to the housing in correlation with an operation of the dose setting button. This provides for an inexpensive mechanical dose setting arrangement.

The piston rod may extend along the main axis and may further comprise a dose setting helical track, and the dose setting element may comprise a dose setting track follower adapted to travel the dose setting helical track corresponding with the operation of the dose setting button. The position of the dose setting element relative to the piston rod can thereby be used to define the axial movement of the piston rod relative to the housing during the subsequent drug expelling action.

The dosing track may be helical, and the dose setting helical track and the dosing track may be opposite-handed and at least partly superposed. Hence, the piston rod may be double threaded, providing a mechanical advantage which reduces the force required to perform a drug expelling action.

The dose setting helical track may be a first non-self-locking thread having a first pitch, and the dosing track may be a second non-self-locking thread having a second pitch. In particular embodiments of the invention the first pitch equals the second pitch.

The dose setting helical track may extend about the piston rod between a proximal helical track end and a distal helical track end, and the track end configuration of the dosing track may be positioned distally of the proximal helical track end. This allows for proximal movement of the dose setting element along the dose setting helical track even when the dosing track follower is at the track end configuration.

The dose expelling mechanism may further comprise a clutch member being rotationally locked to the piston rod and axially movable relative to the housing between a proximal clutch position in which the clutch member is rotationally locked with respect to the housing and a distal clutch position in which the clutch member is free to rotate relative to the housing, an injection button being axially movable relative to the housing between a proximal button position and a distal button position and axially locked with respect to the clutch member such that a) movement of the injection button from the proximal button position to the distal button position causes movement of the clutch member from the proximal clutch position to the distal clutch position and b) movement of the injection button from the distal button position to the proximal button position causes movement of the clutch member from the distal clutch position to the proximal clutch position, and a compression spring arranged to act between an interior surface of the injection button and the dose setting element.

The dose setting mechanism may further comprise a button retaining mechanism capable of retaining the dose setting button in one of a plurality of angular positions relative to the housing when the dose setting button is subjected to a torque below a threshold level, and the compression spring may be dimensioned to apply a force to the dose setting element which causes a torque on the dose setting button below the threshold level.

The mechanical advantage achieved by use of the double threaded piston rod enables use of a single, relatively weak compression spring to force the dose setting element distally relative to the housing during a drug expelling action when the injection button has been moved to the distal button position and the clutch member accordingly has been moved to the distal clutch position. The compression spring causes a translational movement of the dose setting element which due to the first non-self-locking tread connection between the dose setting element and the piston rod and the rotational lock between the piston rod and the clutch member causes the piston rod and the clutch member to rotate. The piston rod is axially movable relative to the clutch member, and the induced rotation of the piston rod is thus converted to a helical advancement relative to the housing by the second non-self-locking thread connection between the piston rod and the housing.

The dose setting member moves axially from a dose setting position to an end-of-dose position during a drug expelling action. The end-of-dose position may e.g. be defined by a dedicated stop surface in, or connected to, the housing. The compression spring also serves to move the injection button from the distal button position to the proximal button position when the user, following a drug expelling action, removes the force applied to the injection button to instigate the dose delivery. A separate return spring for the injection button is thus not needed, further reducing the manufacturing costs of the injection device.

The fact that a compression spring can be used to cause advancement of the piston rod instead of a torsion spring even further reduces the manufacturing costs of the injection device since conventional torsion springs are more expensive to produce, due to the required end hooks, and more cumbersome to handle in the assembly process, due to the need for exact alignment of the respective end hooks with the dedicated geometries of the respective components to which they must be connected.

During a dose increasing dose setting operation of the dose setting button the dose setting element moves proximally along the dose setting helical track, thereby compressing the compression spring. Hence, the compression spring applies an opposite force to the dose setting element, which, due to the fact that the piston rod is prevented from rotating relative to the housing when the clutch member is in the proximal clutch position, seeks to rotate the dose setting element distally along the dose setting helical track. As the dose setting element is rotationally locked with respect to the dose setting button, the dose setting button thereby experiences a torque which the button retaining mechanism serves to resist. The dose setting button can thus be stably positioned in a plurality of angular positions relative to the housing, e.g. corresponding to the number of units settable by one revolution of the dose setting button. The force applied to the dose setting element by the compression spring, and thereby the torque experienced by the dose setting button, is influenced by the design and characteristics of the spring.

In a second aspect of the invention an injection device for delivering a predefined volume of drug from a drug reservoir is provided, the injection device comprising the drug reservoir or means for receiving the drug reservoir, a housing carrying an internal guide member, e.g. a. nut member, and a drug expelling mechanism comprising a piston rod adapted to be displaced relative to the housing to cause an expelling of drug from the drug reservoir, or from a received drug reservoir, the piston rod carrying a track and the internal guide member having a track follower configured for sliding engagement with the track, wherein the track follower is capable of travelling the track from a predetermined pre-use position to a track end configuration during displacement of the piston rod relative to the housing, and wherein a travel from the predetermined pre-use position to the track end configuration corresponds to delivery of the predefined volume of drug.

An injection device is thus provided where a total amount of drug to be delivered from the drug reservoir is predefined by a simple mechanical engagement between the piston rod and the housing, enabling an inexpensive high precision dose delivery device.

The injection device may be adapted to deliver the predefined volume of drug over a plurality of doses, in which case the track follower is adapted to travel the track from the predetermined pre-use position to the track end configuration in a number of steps which correspond to the plurality of doses.

The injection device may further comprise a dose setting mechanism operable to set a dose to be expelled by the dose expelling mechanism, electronic means for registering a dose setting operation, respectively a dose size of an expelled dose, and a display adapted to indicate a size of a current set dose responsive to operations of the dose setting mechanism. The electronic means may be configured to A) determine a current accumulated dose from the dose sizes of registered expelled doses to thereby provide an updated value of a total amount of drug expelled from the reservoir, or from the received reservoir, B) determine a current remaining dose by comparing the current accumulated dose and the predetermined volume of drug, and C) alert the user, via the display, when during a dose increasing operation of the dose setting mechanism the current set dose exceeds the current remaining dose.

The electronic means may be configured to alert the user by freezing the display at the point where the current set dose equals the current remaining dose, e.g. such that the current remaining dose is shown on the display until the user has performed a dose decreasing operation of the dose setting mechanism that brings the current set dose below the current remaining dose. Alternatively, the electronic means may be configured to alert the user by flashing the display, providing additional symbols thereon, or the like.

The injection device is thus able to inform the user safely and discreetly that she or he is setting a dose which exceeds the amount of drug left in the drug reservoir, without having to rely on a mechanical stop interface in the dose setting mechanism that can withstand large forces or torques.

In a particular embodiment of the invention an injection device for delivering a predetermined volume of drug from a cartridge is provided, the injection device comprising the cartridge or means for receiving the cartridge, a housing carrying an internal guide member having a protruding structure, and a drug expelling mechanism accommodated at least partially in the housing and comprising a piston rod adapted to be displaced relative to the housing during drug expelling to cause an expelling of drug from the cartridge, or from a received cartridge, the piston rod having a groove for sliding engagement with the protruding structure, the groove comprising a blocked proximal end constituting a limit, wherein the protruding structure is adapted to travel the groove from a distal end portion to the blocked proximal end during displacement of the piston rod relative to the housing, the travel corresponding to delivery of the predetermined volume of drug.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein FIGS. 4a and 4b are longitudinal section views of a portion of the injection device in another sectional plane, FIG. 5 is a perspective view of a proximal portion of the injection device housing, showing the dose delivery detection mechanism, FIG. 6 is a proximal perspective view of a proximal portion of the injection device housing, FIG. 7 is a cross-sectional view of the injection device, showing the dose setting detection mechanism.

In the figures like structures are mainly identified by like reference numerals.

DESCRIPTION OF EXEMPLARY EMBODIMENTS

When in the following relative expressions, such as "clockwise" and "counter-clockwise", "left" and "right", etc. are used, these refer to the appended figures and not necessarily to an actual situation of use. The shown figures are schematic representations for which reason the configuration of the different structures as well as their relative dimensions are intended to serve illustrative purposes only.

Figure 1:
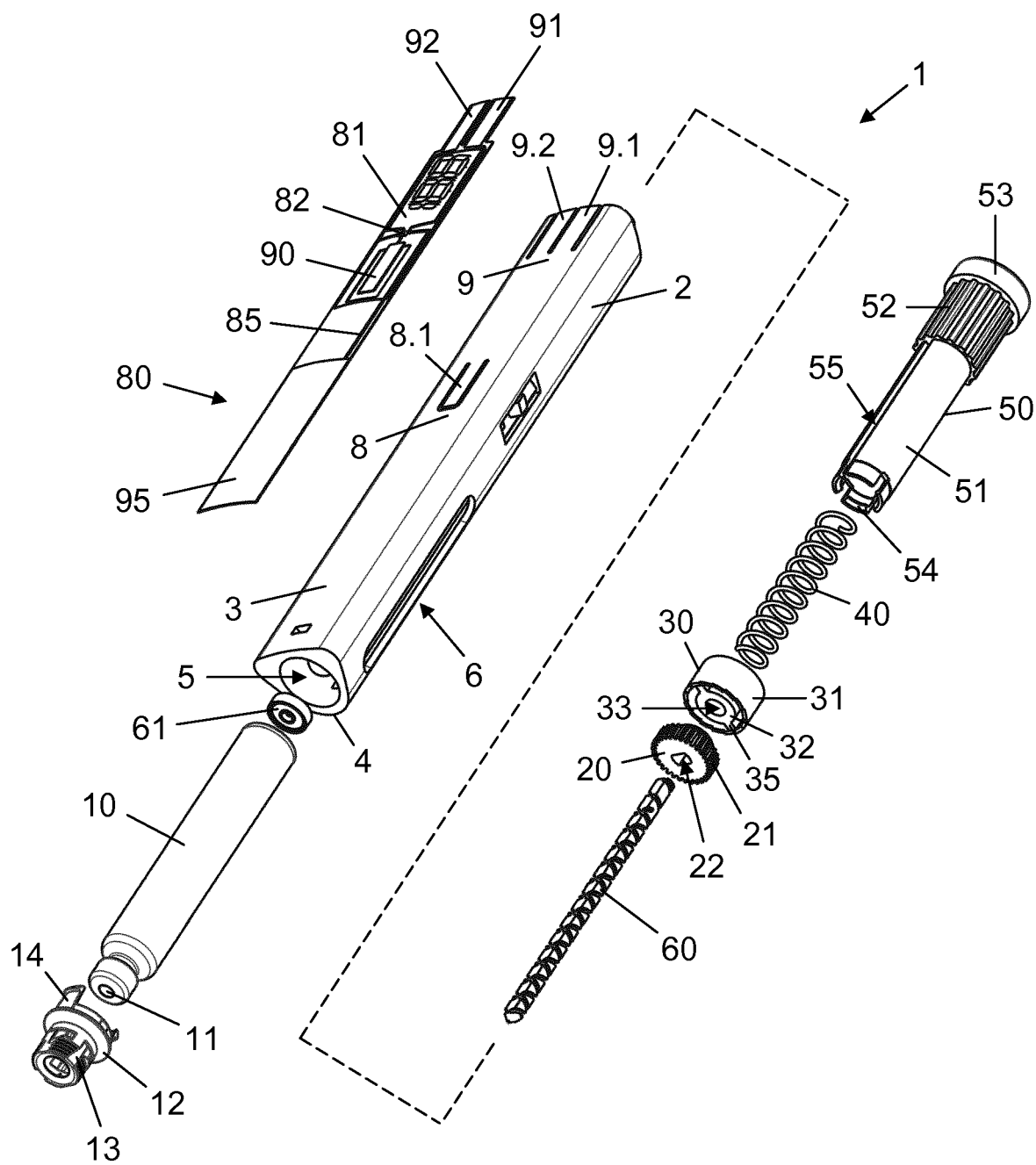
FIG. 1 is an exploded view of an injection device according to an exemplary embodiment of the invention.

FIG. 1 is an exploded view of a pen injection device 1 according to an exemplary embodiment of the invention. The pen injection device 1 comprises a cylindrical housing 2 having a slightly curved information display surface 3 and a more conventionally curved opposing surface 4. The housing 2 accommodates a drug containing cartridge 10, which has been inserted through an opening 5 at a distal end thereof. The cartridge 10, which is closed at its distal end by a penetrable self-sealing septum 11 and at its proximal end by a slidable piston 15 (see FIG. 9), is held within the housing 2 by a cartridge holder 12, being snapped to a proximal interior surface of the housing 2 by a pair of snap arms 14. The cartridge holder 12 further has a needle mount 13 and thereby serves as an attachment interface for an injection needle unit (not shown).

The housing 2 is provided with a longitudinal window 6 for inspection of the cartridge contents and further accommodates both a dose setting mechanism and an injection mechanism. The slidable piston 15 in the cartridge 10 is adapted to be displaced by an elongated dual-threaded piston rod 60 of non-circular cross-section arranged to advance helically through a nut member 17 (see FIG. 3a) forming part of the housing 2. The piston rod 60 exerts a pressure on the slidable piston 15 via a piston washer 61 as a result of being actuated by a setting nut 30, as will be described further below.

The setting nut 30 has an outer annular wall 31 and an inner nut structure 32 with a circular opening 33 for receiving the piston rod 60. The inner nut structure 32 is radially separated from the outer annular wall 31 by an opposing pair of spacer legs 35. A clutch 20 is arranged distally of the setting nut 30 and has a toothed rim 21 and a central opening 22 of non-circular configuration for mating engagement with the piston rod 60, providing a rotational interlocking of the two. The clutch 20 is axially movable within the housing 2 between a proximal dose setting position, in which it is rotationally locked to the housing 2, and a distal dose expelling position, in which it is free to rotate with respect to the housing 2.

A dose dial knob 50 extends into the housing 2 from a proximal end thereof. The dose dial knob 50 comprises a cylindrical main body 51 which is rotatable about a longitudinal axis of the housing 2 by manipulation of an end button 53. A corrugated collar 52 is provided at the main body 51 just distally of the end button 53. The end button 53 has a larger diameter than the main body 51 which serves to limit distal movement of the dose dial knob 50 relative to the housing 2. A number of hooked fingers 54 are provided at the distal end of the main body 51 for engagement with a hooked stub 23 (see FIG. 3a) on the clutch 20, providing an axially interlocking connection between the dose dial knob 50 and the clutch 20. A pair of opposing slots 55 extends longitudinally from the corrugated collar 52 to the hooked fingers 54. Each slot 55 is adapted to receive one of the spacer legs 35, providing a rotationally interlocked, but axially free, connection between the dose dial knob 50 and the setting nut 30.

A compression spring 40 is arranged to act between an interior surface of the end button 53 and a proximal surface of the setting nut 30.

With respect to the housing 2 in a central area 8 of the information display surface 3 some wall material has been removed to provide a radially deflectable central cantilever arm 8.1 and in a proximal area 9 of the information display surface 3 more wall material has been removed to provide a forward indicating radially deflectable proximal cantilever arm 9.1 and a backward indicating radially deflectable proximal cantilever arm 9.2.

A flexible label 80 is adhered to the information display surface 3. The label 80 carries printed electronics in the form of a display 81, a chip 82 comprising a processor and a memory module, a central piezo sensor 90, a first proximal piezo sensor 91, a second proximal piezo sensor 92, a battery 95, and various leads 85 electrically connecting the chip 82 with each of the other electronic components. The label 80 is mounted on the information display surface 3 such that the central piezo sensor 90 is positioned on the central cantilever arm 8.1, the first proximal piezo sensor 91 is positioned on the forward indicating radially deflectable proximal cantilever arm 9.1, and the second proximal piezo sensor 92 is positioned on the backward indicating radially deflectable proximal cantilever arm 9.2.

Figure 2:
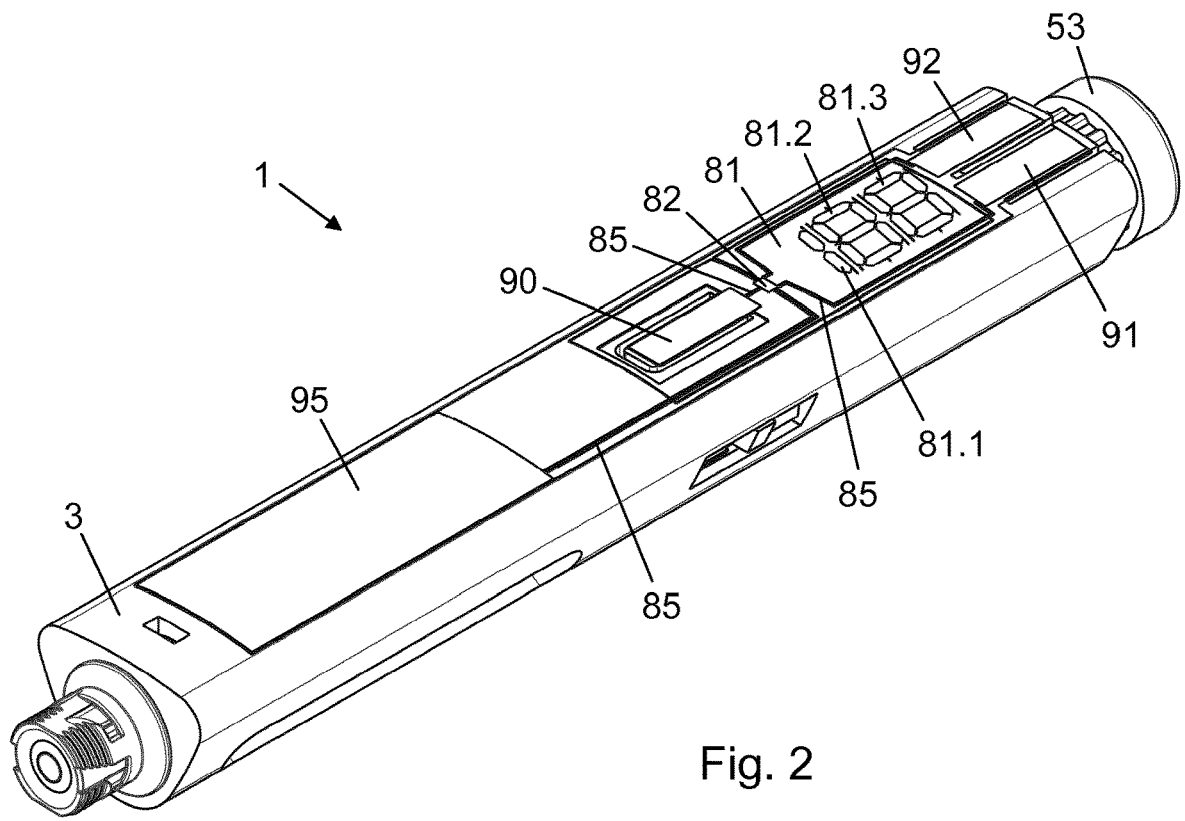
FIG. 2 is a perspective view of the injection device of FIG. 1, FIGS. 3a and 3b are longitudinal section views of a portion of the injection device showing, respectively, the injection device in a state just before setting of the first dose to be delivered and in a state just after delivery of the first dose, before release of the injection button.

FIG. 2 shows the pen injection device 1 in an assembled state detailing the label 80 adhered to the information display surface 3. The display 81 is a 16-segment electrochromic display comprising a 2-segment hundreds digit 81.1 and two 7-segment tens, respectively units digits 81.2, 81.3. The display 81 is capable of showing dose numbers in the range [0 units; 199 units], controlled by the chip 82. The central piezo sensor 90 is bent during a radial deflection of the central cantilever arm 8.1 and will resultantly emit a short peak signal which is detected by the chip 82. Similarly, the first proximal piezo sensor 91 is bent during a radial deflection of the forward indicating radially deflectable proximal cantilever arm 9.1 and the second proximal piezo sensor 92 is bent during a radial deflection of the backward indicating radially deflectable proximal cantilever arm 9.2, each proximal piezo sensor 91, 92 emitting a signal to the chip 82 in response to being bent. The voltage output from any of the piezo sensors is sufficient to wake the processor in the chip 82.

Figure 3A:
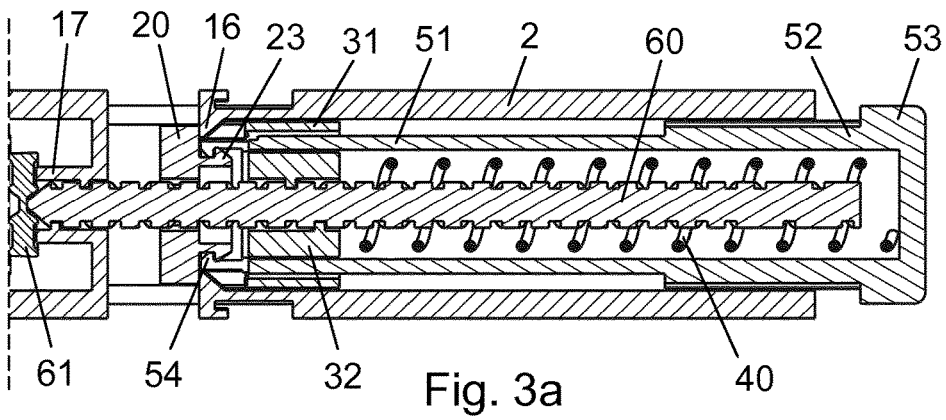
Figure 3B:
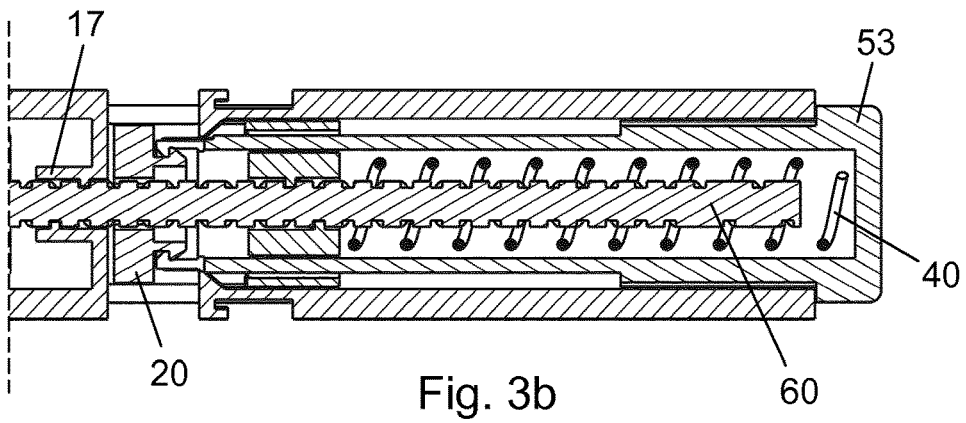

FIGS. 3a and 3b are both longitudinal section views of (approximately) the proximal half of the pen injection device 1, respectively just before setting of the first dose and just after completed expelling of the first dose. FIG. 4a is a longitudinal section view in another sectional plane of a part of the pen injection device 1 in the state shown in FIG. 3a, and FIG. 4b is, similarly, a longitudinal section view in another sectional plane of a part of the pen injection device 1 in the state shown in FIG. 3b.

Hence, FIGS. 3a and 4a show the interrelated positions of the various components in a dose setting state of the pen injection device 1. Specifically, it can be seen from FIG. 3a that in the dose setting state the end button 53 is axially spaced apart from the proximal end of the housing 2 by the compression spring 40, and that the interface between the hooked fingers 54 and the hooked stub 23 accordingly maintains the clutch 20 in the proximal dose setting position. In this position the clutch 20 is rotationally locked with respect to the housing 2 due to an engagement between the toothed rim 21 and a number of longitudinal splines 18 (see FIG. 4*a*) formed internally in the housing. The clutch 20 is prevented from further proximal displacement beyond this position by a stop surface 16 in the housing 2.

FIGS. 3*b* and 4*b*, on the other hand, show the interrelated positions of the various components in a drug expelling state of the pen injection device 1, more particularly at the end of a drug expelling action performed by the drug expelling mechanism, and while the end button 53 is depressed against the housing 2 (see FIG. 3*b*). It is noted that in such a depressed state of the dose dial knob 50 the hooked fingers 54 have forced the clutch 20 into the distal dose expelling position, where the toothed rim 21 is disengaged from the splines 18 (see FIG. 4*b*). It is also noted that at the end of a drug expelling action the outer annular wall 31 of the setting nut 30 rests against an end-of-dose stop 19 in the housing 2, constituted by respective proximal end surfaces of the splines 18 (see FIG. 4*b*).

FIG. 5 is a perspective view cross-sectioned to illustrate the interaction between the clutch 20 and the central cantilever arm 8.1 during a drug expelling action. When the clutch 20 rotates in the dose expelling position the toothed rim 21 moves along an interior wall surface of the housing 2 and as a tooth on the toothed rim 21 passes an inwardly directed protrusion 8.2 on the central cantilever arm 8.1 the central cantilever arm 8.1 is deflected radially outwardly and back, producing a click. The angular displacement of the clutch 20 is correlated with the amount of drug expelled, due to the rotational interlocked relationship between the clutch 20 and the piston rod 60, and in this embodiment each such returned deflection of the central cantilever arm 8.1 corresponds to one incremental unit of drug having been expelled.

FIG. 6 is a perspective view of the proximal end portion of the housing 2 showing interior wall portions of the proximal cantilever arms 9.1, 9.2. It can be seen that the forward indicating radially deflectable proximal cantilever arm 9.1 is provided with an inwardly directed protrusion 9.3 and the backward indicating radially deflectable proximal cantilever arm 9.2 is provided with another inwardly directed protrusion 9.4.

FIG. 7 is a cross-sectional view of the pen injection device 1 through a proximal end portion, illustrating the interaction between the corrugated collar 52 and the proximal cantilever arms 9.1, 9.2 during a dose setting action. As the corrugated collar 52 forms part of the dose dial knob 50 a rotation of the end button 53 causes a corresponding rotation of the corrugated collar 52. In the relative positions of the corrugated collar 52 and the housing 2 shown in FIG. 7 a central ridge 52.0 is positioned between the inwardly directed protrusions 9.3, 9.4, while a first left ridge 52.1 immediately to the left of the central ridge 52.0 is positioned adjacent to a left flank of the inwardly directed protrusion 9.3 and a first right ridge 52.2 immediately to the right of the central ridge 52.0 is positioned adjacent to a right flank of the inwardly directed protrusion 9.4.

A clockwise rotation of the end button 53 from this position will cause firstly the first left ridge 52.1 to start passing the inwardly directed protrusion 9.3, thereby deflecting the forward indicating radially deflectable proximal cantilever arm 9.1, and immediately thereafter the central ridge 52.0 to start passing the inwardly directed protrusion 9.4, thereby deflecting the backward indicating radially deflectable proximal cantilever arm 9.2.

Conversely, a counter-clockwise rotation of the end button 53 from the shown position will cause firstly the first right ridge 52.2 to start passing the inwardly directed protrusion 9.4, thereby deflecting the backward indicating radially deflectable proximal cantilever arm 9.2, and immediately thereafter the central ridge 52.0 to start passing the inwardly directed protrusion 9.3, thereby deflecting the forward indicating radially deflectable proximal cantilever arm 9.1. Each time a ridge on the corrugated collar 52 passes one of the inwardly directed protrusions 9.3, 9.4 a click is produced.

The angular displacement of the dose dial knob 50 is correlated with the axial displacement of the setting nut 30, due to the engagement between the respective spacer legs 35 and slots 55 and a threaded connection between the nut structure 32 and the piston rod 60, and thereby determines the dose set for delivery. In this embodiment each unique pair of deflections of the proximal cantilever arms 9.1, 9.2 caused by two neighbouring ridges on the corrugated collar 52 passing a respective one of the inwardly directed protrusions 9.3, 9.4 in succession corresponds to a change of the set dose by one incremental unit.

In other words, if for example the end button 53 is rotated clockwise from the position shown in FIG. 7 a change of the dose by one unit occurs when the first left ridge 52.1 has passed the inwardly directed protrusion 9.3 and the central ridge 52.0 has subsequently passed the inwardly directed protrusion 9.4, the angular displacement of these two ridges having produced a first forward indicating unique pair of deflections of the proximal cantilever arms 9.1, 9.2. Further clockwise rotation of the end button 53 will cause another change of the dose by one unit to occur when a second left ridge 52.3 immediately to the left of the first left ridge 52.1 has passed the inwardly directed protrusion 9.3 and the first left ridge 52.1 has subsequently passed the inwardly directed protrusion 9.4, the angular displacement of these two ridges having produced a second forward indicating unique pair of deflections of the proximal cantilever arms 9.1, 9.2, and so forth.

On the other hand, if the end button 53 is rotated counter-clockwise from the position shown in FIG. 7 a change of the dose by one unit occurs when the first right ridge 52.2 has passed the inwardly directed protrusion 9.4 and the central ridge 52.0 has subsequently passed the inwardly directed protrusion 9.3, the angular displacement of these two ridges having produced a first backward indicating unique pair of deflections of the proximal cantilever arms 9.1, 9.2. Further counter-clockwise rotation of the end button 53 will cause another change of the dose by one unit to occur when a second right ridge 52.4 immediately to the right of the first right ridge 52.2 has passed the inwardly directed protrusion 9.4 and the first right ridge 52.2 has subsequently passed the inwardly directed protrusion 9.3, the angular displacement of these two ridges having produced a second backward indicating unique pair of deflections of the proximal cantilever arms 9.1, 9.2, and so forth.

Specifically, each forward indicating unique pair of deflections causes an incremental increase of the set dose by one unit and each backward indicating unique pair of deflections causes an incremental decrease of the set dose by one unit.

Figure 8:
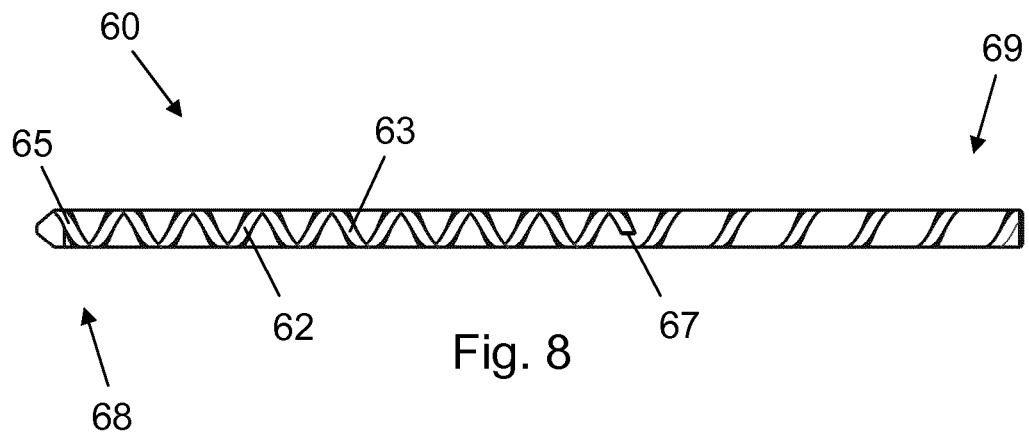
FIG. 8 is a side view of the piston rod employed in the injection device.

FIG. 8 is a side view of the piston rod 60, detailing the configuration of the helical tracks on its exterior surface. The piston rod 60 comprises a non-self-locking dosing thread 63, which mates with a thread in the nut member 17 and an overlapping oppositely handed non-self-locking dose setting thread 62 which mates with a thread in the nut structure 32, providing a mechanical advantage of 2:1.

The non-self-locking dose setting thread 62 extends over the whole length of the piston rod, from a distal end portion 68 to a proximal end portion 69, whereas the non-self-locking dosing thread 63 extends from a thread entrance 65 at the distal end portion 68 to a thread end 67 between the distal end portion 68 and the proximal end portion 69. The helical movement of the piston rod 60 through the nut member 17 is thus limited by the length of the non-self-locking dosing thread 63, and the realisable axial displacement of the piston rod 60 relative to the housing 2, and thereby of the piston 15 in the cartridge 10, is accordingly well-defined.

Figure 9:
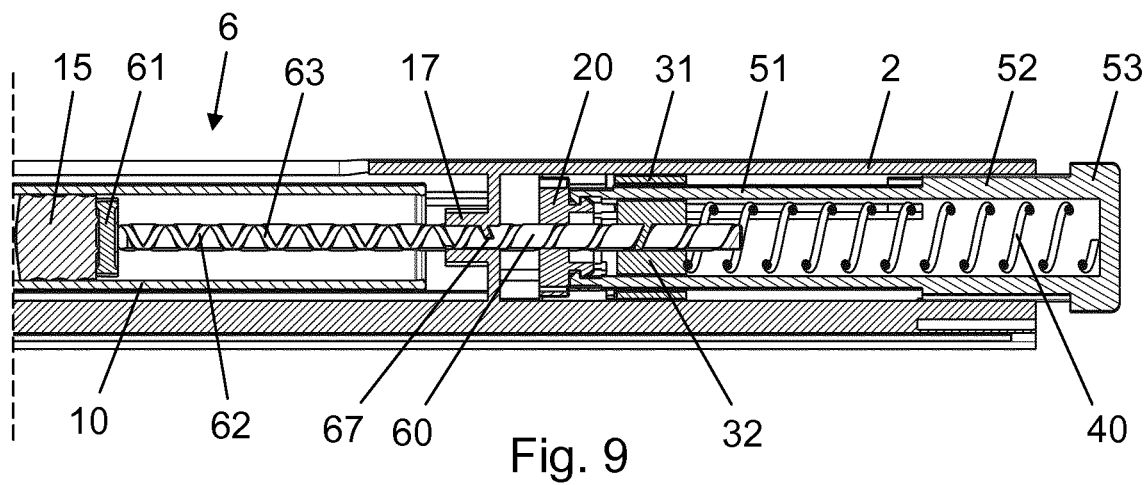
FIG. 9 is a longitudinal section view of a portion of the injection device in a state where the entire expellable volume of drug has been delivered from the drug cartridge.

FIG. 9 shows, in a longitudinal section view, a portion of the pen injection device 1 after delivery of the very last dose of drug from the cartridge 10. The piston rod 60 is fully advanced relative to the cartridge 10, as the thread in the nut member 17 has reached the thread end 67 following a plurality of drug expelling actions. The piston rod 60 is now unable to rotate any further, preventing further advancement of the piston 15 in the cartridge 10. Hence, this represents an end-of-content state of the pen injection device 1.

In the following the invention will be described in connection with a use of the pen injection device 1 according to the present embodiment.

In FIG. 2 the pen injection device 1 is in the dose setting state, where the end button 53 is axially spaced apart from the housing 2. In this state a dose to be delivered from the cartridge 10 is set by the user rotating the end button 53 about the longitudinal axis.

Due to the rotationally interlocked relationship between the setting nut 30 and the dose dial knob 50 the nut structure 32 will travel proximally along the non-self-locking dose setting thread 62 of the piston rod 60 when the end button 53 is rotated clockwise (seen from the proximal end of the pen injection device 1) in a dial up action, the clutch 20 in its dose setting position preventing the piston rod 60 from rotation relative to the housing 2. The proximal displacement of the setting nut 30 will compress the compression spring 40 which thereby stores energy.

The dose dial knob 50 is prevented from rotating in the absence of a user induced torque to the end button 53 due to the engagement between the corrugated collar 52 and the respective inwardly directed protrusions 9.3, 9.4, even when the compression spring 40 experiences a maximum in-use compression. An unintended distal return displacement of the setting nut 30 caused by a prematurely expanding compression spring 40 is thereby prevented. Hence, as long as the clutch 20 is in its dose setting position, where the piston rod 60 is prevented from rotating, the setting nut 30 cannot perform a translational motion with respect to the housing 2 and can only perform a helical distal motion along the non-self-locking dose setting thread 62, if the user rotates the end button 53 counter-clockwise in a dial down action. The compression spring 40 thus remains compressed when the user has completed the dose setting action.

In accordance with the setting nut 30 moving along the non-self-locking dose setting thread 62 of the piston rod 60 the ridges on the corrugated collar 52 passes the respective inwardly directed protrusions 9.3, 9.4, causing deflections of the forward indicating radially deflectable proximal cantilever arm 9.1 and the backward indicating radially deflectable proximal cantilever arm 9.2, as described above. At each deflection of the forward indicating radially deflectable proximal cantilever arm 9.1 the first proximal piezo sensor 91 emits a first sensor signal and at each deflection of the backward indicating radially deflectable proximal cantilever arm 9.2 the second proximal piezo sensor 92 emits a second sensor signal.

Each forward indicating unique pair of deflections in accordance with the above described thus prompts a forward indicating unique signal pair, $SP_f$, consisting of a first sensor signal followed by a second sensor signal. The chip 82 is configured to update the display 81 by an incremental increase in the form of a unit being added to the currently displayed number immediately upon registration of such a forward indicating unique signal pair.

Correspondingly, each backward indicating unique pair of deflections in accordance with the above described prompts a backward indicating unique signal pair, $SP_b$, consisting of a second sensor signal followed by a first sensor signal, and the chip 82 is configured to update the display 81 by an incremental decrease in the form of a unit being subtracted from the currently displayed number immediately upon registration of such a backward indicating unique signal pair. The display 81 accordingly provides a real-time electronic visual indication of the set dose.

A depression of the end button 53 against the housing 2 to expel a set dose (see FIG. 3b) causes the hooked fingers 54 to urge the clutch 20 distally into its dose expelling position, thereby disengaging the toothed rim 21 from the splines 18 (see FIG. 4b) and releasing the compression spring 40. The stored energy therefrom pushes the setting nut 30 distally, and the resulting translational motion of the nut structure 32 causes the piston rod 60 and the clutch 20 to rotate. The piston rod 60 is thus advanced helically through the nut member 17 which causes the piston washer 61 to advance the piston 15 in the cartridge 10, thereby expelling the set dose of drug through an attached injection needle (not shown).

The drug expelling continues until the outer annular wall 31 abuts the end-of-dose stop 19 at which point the piston rod 60, and thereby also the clutch 20, stops rotating. In accordance with the angular displacement of the clutch 20 during the drug expelling action the teeth of the toothed rim 21 pass the inwardly directed protrusion 8.2, causing deflections of the central cantilever arm 8.1, as described above. At each deflection of the central cantilever arm 8.1 the central piezo sensor emits a central sensor signal, $S_c$, and the chip 82 is configured to update the display 81 by an incremental decrease in the form of a unit being subtracted from the currently displayed number immediately upon registration of such a central sensor signal. The display 81 accordingly also provides a real-time electronic visual indication of the dose of drug being expelled.

During a normally progressing dose delivery the display 81 will show a dose count-down until the outer annular wall 31 reaches the end-of-dose stop 19 and the clutch 20 stops rotating, at which point a '0' or some other indication of a completed drug expelling action will be displayed. However, the chip 82 is further configured to update the display 81 to display an error indication, such as e.g. '- -', in case the number of received central sensor signals does not equal the number of registered forward indicating unique signal pairs minus the number of backward indicating unique signal pairs, i.e. in case $\Sigma S_c \neq \Sigma SP_f - \Sigma SP_b$.

For every normally progressing dose delivery (where $\Sigma S_c = \Sigma SP_f - \Sigma SP_b$) the chip 82 is configured to store a value representing the size of the dose delivered and a corresponding time of delivery. The stored data may be forwarded to, or requested by, an exterior device (not shown) via e.g. a wireless communication link (not shown).

As is clear from the above during each drug expelling action the piston rod 60 moves helically relative to the housing 2 in accordance with the size of the dose delivered, and the thread in the nut member 17 thereby travels the non-self-locking dosing thread 63 a certain distance. So, after a plurality of drug expelling actions the piston rod 60 has undergone an accumulated displacement relative to the housing 2 which is correlated with the sum of doses that have been delivered. In accordance therewith the thread in the nut member 17 has increasingly approached the thread end 67.

The chip 82 is configured to calculate, following each drug expelling action, a current accumulcted dose as a sum of stored dose sizes to thereby keep track of the total amount of drug delivered from the cartridge 10. Furthermore, the chip 82 is pre-programmed with information of the total amount of drug available from the cartridge 10 prior to use, and is also configured to calculate a current remaining dose as a subtraction of the current accumulated dose from the total amount of drug available. In other words, the chip 82 repeatedly determines and stores the amount of drug left in the cartridge 10 during the lifetime of the pen injection device 1.

When the cartridge 10 is near empty and the user operates the dose dial knob 50 to set a dose the chip 82 prompts the display 81 to update the count accordingly, as described above. However, if during a dose increasing operation of the dose dial knob 50 the set dose suddenly exceeds the amount of drug left in the cartridge 10, as determined and stored by the chip 82, the chip 82 stops updating the display 81. Any further dose increasing operations of the dose dial knob 50 will not result in a change to the display 81, which is frozen in a state where it provides a visual indication of the amount of drug left to be delivered. Importantly, though, the deflections of the proximal cantilever arms 9.1, 9.2 due to the subsequent angular displacement of the corrugated collar 52 are registered, even though no visual update is provided. Thus, if the user decides to decrease the set dose then the chip 82 will detect when the size of the set dose falls below the amount of drug left in the cartridge 10 and will consequently again update the display 81.

During the dose setting operation the setting nut 30 travels the non-self-locking dose setting thread 62 in correlation with the angular displacement of the main body 51. However, the setting nut 30 will not meet a physical stop surface when the set dose equals the amount of drug left in the cartridge 10, so the user will not be able to cause breakage of any internal components in the pen injection device 1 by applying a greater torque to the dose dial knob 50. The end-of-content user interface is electronic rather than mechanical, as the chip 82 governs the information relay completely. The chip 82 is in control of how much remains to be expelled from the cartridge 10, and the pen injection device 1 thus provides a visual indication of the fact that a dose limit has been reached during dose setting instead of a tactile stop.

It is the position of the piston rod 60 relative to the nut member 17 that eventually determines the end-of-content state of the pen injection device 1, not the position of the setting nut 30 relative to the piston rod 60. Hence, even if the user in principle sets a larger dose than the amount of drug left in the cartridge 10 by rotating the dose dial knob 50 in a dose increasing direction after the dose count on the display 81 has stopped, it is the amount of drug left in the cartridge 10 that will be delivered during the following drug expelling action because that amount is correlated with the remaining travel of the thread in the nut member 17 to the thread end 67. Notably, since the chip 82 has frozen the display 81 at the dose limit the actually delivered amount of drug will correspond to the dose shown on the display 81.

The invention claimed is:

1. An injection device for delivering multiple doses of drug, comprising:
   a housing extending along a main axis,
   a dose expelling mechanism comprising a piston rod configured to move relative to the housing from a first position to a second position to cause ejection of a dose of drug, the piston rod extending between a proximal piston rod end and a distal piston rod end and comprising a dosing track, the piston rod further being movable relative to the housing from an initial pre-use position to a final end stop position to cause accumulated ejection of a predefined total dose,
   a dosing track follower fixed with respect to the housing and adapted to travel the dosing track during dose ejection,
   a dose setting mechanism operable to set the dose to be ejected by the dose expelling mechanism,
   electronic structure for registering a dose setting operation and for registering a dose size of an ejected dose, and
   a display adapted to indicate a size of a current set dose, the electronic structure being configured to provide a first type of update of the display responsive to dose changing operations of the dose setting mechanism,
   wherein the electronic structure is further configured to
      calculate a current accumulated dose from the dose sizes of registered ejected doses to thereby provide an updated value of a total amount of drug ejected,
      determine a current remaining dose by comparing the current accumulated dose and the predefined total dose, and
      provide a second type of update of the display when during a dose increasing operation of the dose setting mechanism the current set dose exceeds the current remaining dose, the second type of update being different from the first type of update, and
   wherein the final end stop position is defined by a track end configuration of the dosing track between the proximal piston rod end and the distal piston rod end arranged at a specific position along the piston rod which correlates an accumulated travel of the dosing track follower from a predetermined pre-use position in or on the dosing track to the track end configuration with an expelling of the predefined total dose.

2. The injection device according to claim 1, wherein the dose setting mechanism comprises a user operable dose setting button and a dose setting element rotationally locked with respect to the dose setting button and adapted to undergo helical movement relative to the housing in correlation with an operation of the dose setting button.

3. The injection device according to claim 2, wherein the piston rod extends along the main axis and further comprises a dose setting helical track, and wherein the dose setting element comprises a dose setting track follower adapted to travel the dose setting helical track corresponding with the operation of the dose setting button.

4. The injection device according to claim 3, wherein the dosing track is helical, and the dose setting helical track and the dosing track are opposite-handed and at least partly superposed.

5. The injection device according to claim 4, wherein the dose setting helical track is a first non-self-locking thread having a first pitch, and the dosing track is a second non-self-locking thread having a second pitch, and wherein the first pitch equals the second pitch.

6. The injection device according to claim 5, wherein the dose expelling mechanism further comprises:
- a clutch member being rotationally locked to the piston rod and axially movable relative to the housing between a proximal clutch position in which the clutch member is rotationally locked with respect to the housing and a distal clutch position in which the clutch member is free to rotate relative to the housing,
- an injection button being axially movable relative to the housing between a proximal button position and a distal button position and axially locked with respect to the clutch member such that a) movement of the injection button from the proximal button position to the distal button position causes movement of the clutch member from the proximal clutch position to the distal clutch position and b) movement of the injection button from the distal button position to the proximal button position causes movement of the clutch member from the distal clutch position to the proximal clutch position, and
- a compression spring arranged to act between an interior surface of the injection button and the dose setting element, wherein the dose setting mechanism further comprises a button retaining mechanism capable of retaining the dose setting button in one of a plurality of angular positions relative to the housing when the dose setting button is subjected to a torque below a threshold level, and wherein the compression spring is dimensioned to apply a force to the dose setting element which causes a torque on the dose setting button below the threshold level.

7. The injection device according to claim 1, wherein the second type of update comprises a freeze of the indication of the size of the current set dose.

8. The injection device according to claim 1, wherein the second type of update comprises a change of form, position and/or colour of the indication of the size of the current set dose relative to previously displayed indications of the size of the current set dose.

9. The injection device according to claim 1, wherein the second type of update comprises an enabling of an otherwise disabled symbol on the display.

10. The injection device according to claim 1, wherein the second type of update comprises an indicator being alternatingly visible and invisible.

11. The injection device according to claim 1, wherein the electronic structure is further configured to provide the first type of update of the display when during a dose decreasing operation of the dose setting mechanism the current set dose falls below the current remaining dose.

* * * * *

UNITED STATES PATENT AND TRADEMARK OFFICE
CERTIFICATE OF CORRECTION

| | | |
|---|---|---|
| PATENT NO. | : 11,400,227 B2 | Page 1 of 1 |
| APPLICATION NO. | : 16/500991 | |
| DATED | : August 2, 2022 | |
| INVENTOR(S) | : Jakobsen | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 113 days.

Signed and Sealed this
Tenth Day of June, 2025

Coke Morgan Stewart
*Acting Director of the United States Patent and Trademark Office*